United States Patent
Bornzin

(10) Patent No.: US 10,661,085 B2
(45) Date of Patent: May 26, 2020

(54) ANTI-TACHYCARDIA PACING FOR LOW POWER IMPLANTABLE MEDICAL DEVICES

(71) Applicant: PACESETTER, INC., Sylmar, CA (US)

(72) Inventor: Gene A. Bornzin, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 270 days.

(21) Appl. No.: 15/829,290

(22) Filed: Dec. 1, 2017

(65) Prior Publication Data
US 2019/0167993 A1    Jun. 6, 2019

(51) Int. Cl.
*A61N 1/36*    (2006.01)
*A61N 1/362*    (2006.01)
(Continued)

(52) U.S. Cl.
CPC ........ *A61N 1/3622* (2013.01); *A61B 5/04012* (2013.01); *A61B 5/0464* (2013.01); *A61B 5/6847* (2013.01); *A61B 5/6869* (2013.01); *A61B 5/7235* (2013.01); *A61B 5/7282* (2013.01); *A61N 1/3621* (2013.01);
(Continued)

(58) Field of Classification Search
CPC .............. A61N 1/3622; A61N 1/39622; A61N 1/37512; A61N 1/3621; A61N 1/3704; A61N 1/3756; A61N 1/378; A61N 1/0573; A61N 1/059; A61N 1/365; A61N 1/3702; A61N 1/3708; A61N 2001/083;
(Continued)

(56) References Cited

U.S. PATENT DOCUMENTS 6,731,982 B1 * 5/2004 Kroll ................. A61N 1/36185
607/14
2006/0100670 A1   5/2006 Sweeney
(Continued)

FOREIGN PATENT DOCUMENTS

EP         1758645 A1    3/2007

OTHER PUBLICATIONS

European Search Report dated Mar. 1, 2019; Application No. 18209360.9.

*Primary Examiner* — Catherine M Voorhees
*Assistant Examiner* — Roland Dinga
(74) *Attorney, Agent, or Firm* — Dean D. Small; The Small Patent Law Group, LLC

(57) ABSTRACT

Methods and devices are provided for managing anti-tachycardia pacing therapy delivered by an implantable medical device (IMD). The methods and devices detect events from cardiac signals sensed at electrodes of the IMD. The cardiac signals represent a ventricular tachycardia (VT) episode that includes at least a select number of VT events having a corresponding VT cycle length. The methods and devices analyze the VT cycle length to define an anti-tachycardia pacing (ATP) therapy that includes a first coupling interval and deliver a first ATP pulse that is spaced the first coupling interval after a reference refractory VT event sensed at the electrodes. The methods and devices deliver a second ATP pulse following the first ATP pulse by a non-stimulation segment that is at least one and three-quarters (1.75) times a projected VT cycle length.

12 Claims, 8 Drawing Sheets

(51) Int. Cl.
*A61B 5/04* (2006.01)
*A61B 5/00* (2006.01)
*A61B 5/0464* (2006.01)
*A61N 1/39* (2006.01)
*A61N 1/375* (2006.01)
*A61N 1/37* (2006.01)
*A61N 1/378* (2006.01)
*A61N 1/365* (2006.01)
*A61N 1/05* (2006.01)
*A61N 1/08* (2006.01)

(52) U.S. Cl.
CPC .......... *A61N 1/3704* (2013.01); *A61N 1/378* (2013.01); *A61N 1/3756* (2013.01); *A61N 1/37512* (2017.08); *A61N 1/39622* (2017.08); *A61N 1/059* (2013.01); *A61N 1/0573* (2013.01); *A61N 1/365* (2013.01); *A61N 1/3702* (2013.01); *A61N 1/3708* (2013.01); *A61N 2001/083* (2013.01)

(58) Field of Classification Search
CPC . A61B 5/04012; A61B 5/0464; A61B 5/6869; A61B 5/7235; A61B 5/7282
See application file for complete search history.

(56) References Cited

U.S. PATENT DOCUMENTS

2017/0209696 A1\* 7/2017 Kaiser .................. A61N 1/3622
2017/0312516 A1   11/2017 Jackson et al.

\* cited by examiner

ANTI-TACHYCARDIA PACING FOR LOW POWER IMPLANTABLE MEDICAL DEVICES

BACKGROUND

Embodiments of the present disclosure generally relate to methods and devices for anti-tachycardia pacing, and more particularly to delivery of anti-tachycardia pacing therapy by a low-power implantable medical device (IMD).

Ventricular tachycardia may be controlled through electrical therapy delivered by an implanted medical device, such as a pacemaker, implantable cardioverter defibrillator and the like. The device applies an electric stimulation to the heart muscle to interrupt or disrupt the fast rhythm. The electric stimulation may be in the form of timed pacemaker pulses or by high voltage shock. Anti-tachycardia pacing (ATP) has been used to convert a ventricular tachycardia into a normal sinus rhythm. Tachycardia is often the result of electrical feedback within the heart, wherein a natural beat results in the feedback of an electrical stimulus which prematurely triggers another beat. By interposing a stimulated heartbeat (i.e., a pacing pulse), the stability of the feedback loop is disrupted. For example, patients with monomorphic ventricular tachycardia (MVT) may be successfully paced out of the tachycardia using a rapid burst of high rate pacing. The burst includes a selected number of pulses that are delivered at the same rate, at an accelerating rate, or an alternating accelerating/decelerating rate.

Traditionally, ATP is delivered in bursts, where each burst includes a series of pulses. Several bursts may be given for any tachycardia episode. Following detection or redetection of a tachycardia, the first ATP pulse is delivered synchronously with an intrinsic event while the remaining pulses are delivered in a VOO mode.

Various approaches to ATP therapy have been utilized. For example, conventional ATP bursts may be delivered in accordance with one or more of ramping, scanning, adaptation, and/or a combination thereof. In convention ramped ATP, the ATP bursts are delivered with the interval between successive pulses shortened. In convention ATP scanning, each burst, that is used to treat a tachyarrhythmia event, may be delivered by progressively shortening the cycle length. When the burst cycle length is adjusting based on the intrinsic cycle length, the adjustment in the ATP therapy is called an adaptation. Typically ATP pulses have an amplitude of 7.5 V to 9.0V and have a pulse width of 1.0 to 1.5 ms. The pulses are delivered at intervals ranging from 200 to 550 milliseconds to provide 1.8 to 5 pulses per seconds.

However, conventional ATP therapies experience disadvantages when implemented by IMDs that utilize a low power source. For example, leadless pacemakers and other low power IMDs utilize batteries that are physically very small and exhibit a low initial charge. The leadless pacemakers and other low power IMDs experience a challenge to provide sustained voltages in excess of 6 V for a longer pulse widths (e.g., 0.4 ms) at a high pulse rate (e.g., 160 ppm or spaced at about 375 ms intervals). Instead, during delivery of conventional ATP therapy, the leadless pacemaker experiences a significant voltage drop when delivering ATP. As one example, if a leadless pacemaker utilized a battery that exhibits 1K ohms source impedance at some point in the life of the battery, the leadless pacemaker would experience approximately a 6% drop in pacing voltage (across the electrodes) when delivering a pacing pulse programmed to 6 V amplitude with a pulse width of 1.5 ms when delivering about 4 ATP pulses per second. Furthermore, if a 9 volt pacing pulse is programmed, a 10% drop in pacing amplitude would be expected. The drop in pacing voltage will be greater as the source impedance of the battery increases and battery source impedances for small batteries will increase well above 1 k over the battery's service life.

A need remains for an improved ATP therapy that does not require high rate pacing pulses to provide effective ATP and that affords an ATP therapy that is compatible with leadless pacemakers and other low power IMDs.

SUMMARY

In accordance with embodiments herein, a computer implemented method is provided for managing anti-tachycardia pacing therapy delivered by an implantable medical device (IMD). The method comprises detecting events from cardiac signals sensed at electrodes of the IMD, the cardiac signals representative of a ventricular tachycardia (VT) episode that includes at least a select number of VT events having a corresponding VT cycle length. The method further utilizes one or more processors for analyzing the VT cycle length to define an anti-tachycardia pacing (ATP) therapy that includes a first coupling interval; delivering a first ATP pulse that is spaced the first coupling interval after a reference refractory VT event sensed at the electrodes; and delivering a second ATP pulse following the first ATP pulse by a non-stimulation segment that is at least one and three-quarters (1.75) times a projected VT cycle length.

Optionally, the method may analyze the VT cycle length to determine a secondary delay that is at least twice the VT cycle length and determining a length of the non-stimulation segment based on the secondary delay, such that the non-stimulation segment is at least twice the projected VT cycle length. Optionally, the secondary delay may correspond to a time interval that equals the coupling interval combined with a number N of a projected VT cycle length. Optionally, the number N is two or greater. Optionally, the method further utilizes a power source, in a low charge state, to maintain charge on a charge delivery circuit of the IMD for the ATP therapy, the low-charge state corresponding to the power source having a source impedance equal to or greater than 2000 ohms.

Optionally, the ATP therapy includes at least three ATP pulses having an amplitude of at least 6 V and a pulse width of at least 0.4 ms. Optionally, the first coupling interval may be set to time the first ATP pulse to occur during a non-refractory state of tissue proximate to the electrodes of the IMD. Optionally, the method further comprises disabling the sensing circuit for a depolarization interval following delivery of the first ATP pulse, and enabling the sensing circuit to sense cardiac signals after termination of the depolarization interval and before delivery of the second ATP pulse. Optionally, the method may include determining an ending point of the non-stimulation segment based on a second coupling interval related to a VT cycle length of at least two VT events that occur after delivery of the first ATP pulse.

In accordance with the embodiments herein, an implantable medical device is provided. The IMD comprises a housing coupled to electrodes; an power source within the housing; memory, within the housing, to store storing program instructions; a sensing circuit to sense cardiac signals from the electrodes, the cardiac signals representative of a ventricular tachycardia (VT) episode that includes at least a select number of VT events having corresponding VT cycle lengths; and one or more processors within the housing. Responsive to execution of the program instructions, the one or more processors: analyze the VT cycle length to define an anti-tachycardia pacing (ATP) therapy that includes a first coupling interval; deliver a first ATP pulse that is spaced the coupling interval after a reference refractory VT event sensed at the electrodes; and deliver a second ATP pulse following the first ATP pulse by a non-stimulation segment that is at least one and three-quarters (1.75) times a projected VT cycle length.

Optionally, the power source includes one or more batteries having terminals connected to a charge storage circuit, the power source exhibiting a power state in which a source impedance, across the terminals of the power source, is equal to or greater than 2000 ohms when the power source is connected to a charge storage circuit. Optionally, the implantable medical device may be a leadless pacemaker with the electrodes provided on or as part of the housing.

Optionally, the one or more processors may be configured to analyze the VT cycle length to determine the projected VT cycle length and to determine a secondary delay that is at least twice the projected VT cycle length and determine a length of the non-stimulation segment based on the secondary delay. The secondary delay may correspond to a time interval that equals the coupling interval combined with a number N of the projected VT cycle length. The first coupling interval may be a percentage of the projected VT cycle length.

Optionally, the one or more processors are configured to define the ATP therapy to include at least three ATP pulses having an amplitude of at least 6 V and a pulse width of at least 0.4 ms. The one or more processors may be configured to set the first coupling interval to time the first ATP pulse to occur during a non-refractory state of tissue proximate to the electrodes of the IMD.

Optionally, the sensing circuit is disabled for a depolarization interval following delivery of the first ATP pulse and, after termination of the depolarization interval, the sensing circuit is enabled to sense cardiac signals, between the first and second ATP pulses. Optionally, the one or more processors are configured to time delivery of a second ATP pulse, such that at least two projected VT cycles occur before delivering the second ATP pulse. Optionally, the one or more processors are configured to time delivery of the second ATP pulse based on at least two VT events sensed after termination of the depolarization interval. Optionally, the device may determine a length of the non-stimulation segment based on a second coupling interval related to a VT cycle length of the at least two VT events sensed after termination of the depolarization interval.

DETAILED DESCRIPTION

Figure 1A:
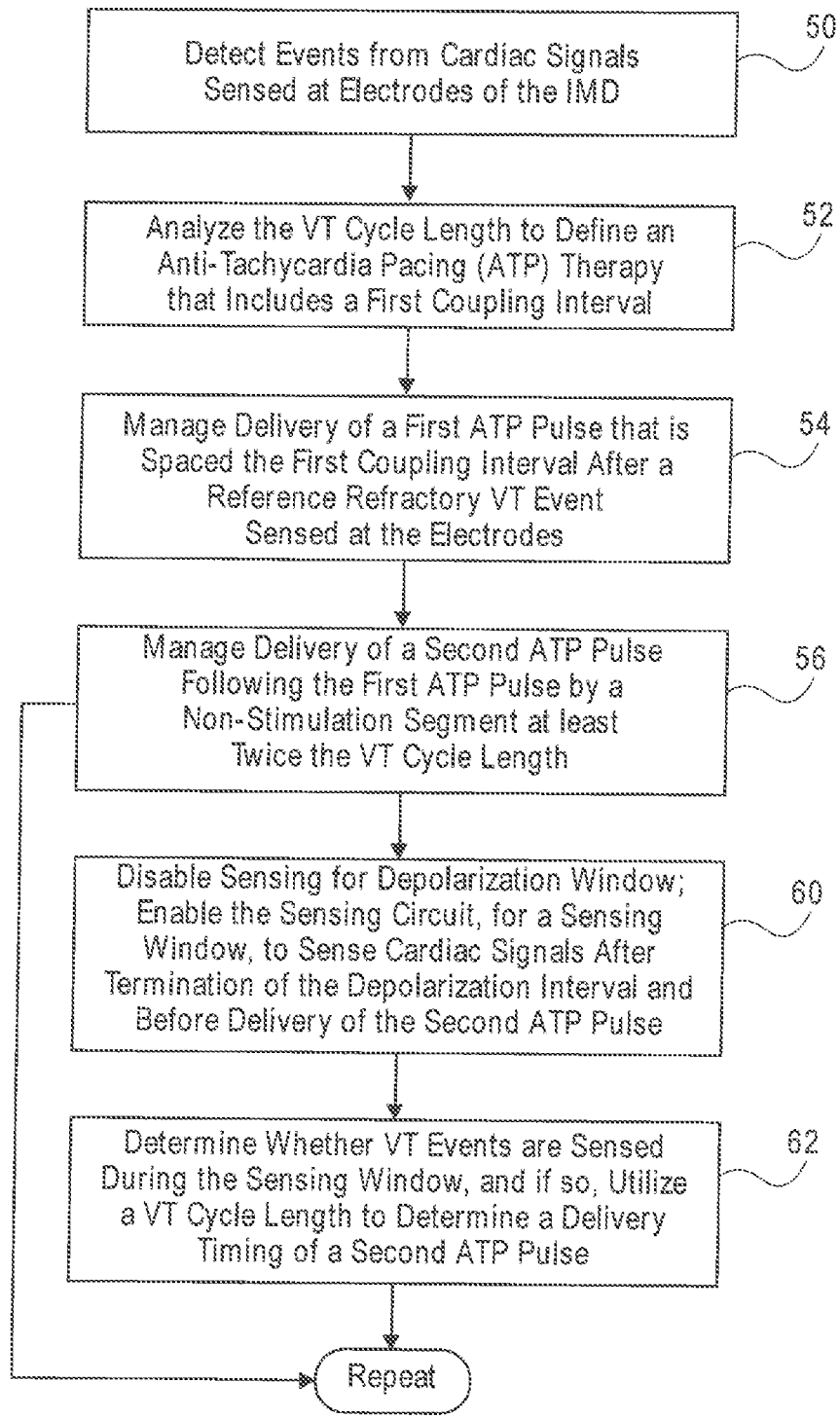
FIG. 1A illustrates a process implemented in accordance with embodiments herein for managing anti-tachycardia pacing therapy delivered by an implantable medical device.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems.

While the operations of some methods may be described as performed by the processor(s) of one device, additionally, some or all of such operations may be performed by the processor(s) of another device described herein. For example, the methods may be implemented by one or more processors of an IMD, executing program instructions stored in memory of the IMD. Additionally or alternatively, the methods may be implemented by one or more processors of an external device, executing program instructions stored in memory of the external device. Additionally or alternatively, the methods may be distributed between processors of an IMD and one or more external devices.

In accordance with embodiments herein, methods and systems are provided that utilize an ATP therapy having fewer pulses than conventional ATP therapies, while still maintaining efficacy. As one example, the efficacy is maintained by coupling the first ATP pulse to a ventricular sensed event and providing secondary ATP pulses having a pulse to pulse spacing according to a spread-pattern that is at least 2 times wider than a projected VT cycle length. In many instances, the ATP therapies herein will have a pulse to pulse interval that is at least two times a conventional ATP therapy pulse to pulse interval. Once the pulses are spaced apart by the spread-pattern, remaining parameters of the timing of the pulses can be established using adaptive, ramp, and/or scanning methods. As one example, the spread-pattern effectively delivers every other pulse, as compared to a conventional ATP therapy.

Additionally, in accordance with embodiments herein, the ATP therapy utilizes a non-marker first ATP pulse. The ATP therapy removes the conventional marker pulse which is previously given synchronously with intrinsic detection. The conventional marker pulse has no therapeutic impact as the conventional marker pulse is delivered, when the cardiac tissue is refractory. In accordance with embodiments herein, the ATP therapy times a first ATP pulse to be coupled to a last ventricular sensed event such that the first ATP pulse occurs while the tissue is in a non-refractory state, followed by secondary pulses. The ATP therapy is delivered with a first ATP pulse coupled to the last sensed ventricular event wherein the coupling interval has a programmable relation to a projected VT cycle length or has an adaptive interval. For example, the IMD delivers the first ATP pulse following a coupling interval that is a percentage of a last measured VT cycle length, e.g. 85%.

Optionally, embodiments herein may perform sensing between at least a portion of the ATP pulses. For example, the IMD may resume sensing at a predetermined time (e.g., a depolarization interval) after delivering the first ATP pulse. Optionally, before delivering secondary ATP pulses, the IMD senses for intrinsic events (e.g., two or more events). If the intrinsic events are separated by an interval that is normal, the IMD need not deliver any additional ATP pulses. However, if the intrinsic events are separated by an interval within a tachycardia range, then the IMD delivers another ATP pulse coupled to a sensed ventricular event. Optionally, the ATP coupling interval may be scanned by decreasing the coupling interval with each ATP attempt to increase a probability of pacing while the tissue is in an excitable state (e.g., not refractory). As one example, the IMD may resume sensing within a depolarization interval of about 100 ms following an ATP pulse, depending on post pacing polarization and sensitivity of the electrodes. Optionally, the IMD may be configured to deliver two or more ATP pulses before opening a sensing window to sense events.

The discussion herein refers, in part, to determination, analysis and other operations that are performed in connection with event cycle lengths. However, it is understood that the operations described in connection with cycle length more generally relate to the events of interest within cardiac cycles. For example, the cardiac events may represent fibrillation events, ventricular tachycardia events or normal-physiologic events. As one example, when an operation in a flowchart is described in connection with determining a cycle length, additionally or alternatively, the operation may involve determining a corresponding event of interest.

Terms

The term "episode" is used to refer to a series of cardiac events that collectively correspond to a physiologic or non-physiologic behavior. For example, a series of cardiac events may include a sufficient number of ventricular tachycardia events to collectively indicate a ventricular tachycardia episode. As another example, a series of cardiac events may include a sufficient number of fibrillation events to collectively indicate a fibrillation episode.

The term "power source" refers to one or more batteries connected in series or parallel. The batteries may be rechargeable or non-rechargeable.

The term "low-charge" refers to a present state of a power source within a leadless or lead-based IMD at any point throughout the operational life of the IMD. The low-charge state of a power source is not only determined when the power source is new. Instead, power sources discharge power over the life of the power source during use. Consequently, a power source that is fully charged may not initially represent a low-charge, power source, but over time becomes a low-charge power source after a certain amount of discharge. The term "low-charge" power source includes both i) new power sources that are fully charged, but exhibit low-charge and ii) used power sources that are in a partially discharged state and exhibit low-charge. The power state of a power source is indicated by the source impedance measured across the terminals of the power source when exposed to the load of the charge storage circuit within the IMD.

As used herein, a power source is in a "low-charge" state when the power source exhibits a source impedance, across the terminals of the power source, equal to or greater than 2000 ohms when the power source is connected to a load of the charge storage circuit within the IMD. Due in part to the small size, the power source in a leadless pacemaker, when relatively new, exhibits limited charge storage and a corresponding source impedance that is equal to or greater than 2000 ohms. The term "low-charge" power source also refers to power sources within lead-based IMDs where the power source has reached a charge storage state that corresponds to a source impedance equal to or greater than 2000 ohms, at the output terminals of the power source. For example, in a lead based pacemaker, the batteries when new will exhibit greater charge storage and a corresponding low source impedance below 2000 ohms. Over the life of the lead based pacemaker, the batteries experience discharge of the charge storage. As the batteries are depleted, the remaining charge storage decreases and the source impedance increases. At some intermediate or late point in the life of the batteries in the lead based pacemaker, the batteries will exhibit a source impedance of 2000 ohms or greater.

The term "ATP therapy" refers to a therapy that is defined to comprise multiple (at least two) ATP pulses that are separated by a non-stimulation segment that is a number N of a projected VT cycle length, where N is any rational number of at least one and three-quarters (1.75). For example, the non-=stimulation segment may be 1.75 times the projected VT cycle length, 1.85 times the projected VT cycle length, 1.95 times the projected VT cycle length, twice the projected VT cycle length, or any other rational number N times the projected VT cycle length. The ATP therapy includes at least first and second ATP pulses, where at least two projected VT cycles occur before delivering the second ATP pulse. However, as explained herein, in embodiments utilizing sensing during the non-stimulation segments, the second and later ATP pulses may not be delivered, when a sensing circuit determines that the second ATP pulse is not warranted or an alternative to therapy is needed. The length of the non-stimulation segment, while being at least one and three-quarters (1.75) times a projected VT cycle length, may be determined in at least two different manners. For example, the length of the non-stimulation segment may be defined to correspond to a secondary delay that combines the coupling interval with a number N of a projected VT cycle length. Alternatively, the length of the non-stimulation segment may be defined based on events sensed by the sensing circuit following the first ATP pulse. For example, following the first ATP pulse (and a depolarization interval) the sensing circuit may detect additional VT events, from which a new VT cycle length (e.g. new projected VT cycle length) is determined. The one or more processors time delivery of the second ATP pulse to follow the second or later additional VT event by a second coupling interval. In this alternative "sensing based" ATP therapy, the second ATP pulse is delivered after the first ATP pulse with at least two intervening VT events.

Non-limiting examples of parameters for the pulses within an ATP therapy include at least three ATP pulses having an amplitude of at least 6 V and a pulse width of at least 0.4 ms. additionally or alternatively, the ATP pulses may have an amplitude of approximately 9.0 V and a pulse width of 1.0 to 1.5 ms.

ATP Process

FIG. 1A illustrates a process implemented in accordance with embodiments herein for managing anti-tachycardia pacing therapy delivered by an implantable medical device. At 50, one or more processors of the IMD and/or sensing circuit detect events from cardiac signals sensed at electrodes of the IMD. The cardiac signals representative of a ventricular tachycardia (VT) episode that includes at least a select number of VT events having a corresponding VT cycle length. At 52, the one or more processors of the IMD analyze the VT cycle length to define an anti-tachycardia pacing (ATP) therapy that includes a first coupling interval. At 54, the one or more processors of the IMD manage delivery of a first ATP pulse that is spaced the first coupling interval after a reference refractory VT event sensed at the electrodes. At 56, the one or more processors of the IMD manage delivering of a second ATP pulse following the first ATP pulse by a non-stimulation segment that is at least one and three-quarters (1.75) times the VT cycle length. As explained here, the non-stimulation segment may be set to correspond to a number N of a projected VT cycle length, where N is any rational number of at least one and three-quarters (1.75). For example, the non-=stimulation segment may be 1.75 times the projected VT cycle length, 1.85 times the projected VT cycle length, 1.95 times the projected VT cycle length, twice the projected VT cycle length, or any other rational number N times the projected VT cycle length. The ATP therapy includes at least first and second ATP pulses. However, as explained herein, in embodiments utilizing sensing during the non-stimulation segments, the second and later ATP pulses may not be delivered, when a sensing circuit determines that the second ATP pulse is not warranted or an alternative to therapy is needed. Thereafter, in accordance with embodiments herein, flow branches to repeat the operations at 50-56.

Optionally, flow may continue from 56 to 60, in accordance with embodiments that perform sensing during the non-stimulation segment. At 60, the one or more processors disable the sensing circuit for a depolarization interval following delivery of the first ATP pulse. After the depolarization interval, the one or more processors enable the sensing circuit, for a sensing window, to sense cardiac signals after termination of the depolarization interval and before delivery of the second ATP pulse. At 62, the one or more processors determine whether VT events are sensed during the sensing window, and if so, utilize a VT cycle length related thereto in connection with determining a delivery timing of a second ATP pulse in the ATP therapy. For example, an ending point of the non-stimulation segment may be set based on a second coupling interval related to a VT cycle length of at least two VT events that occur after delivery of the first ATP pulse.

Optionally, the first coupling interval is set to time the first ATP pulse to occur during a non-refractory state of tissue proximate to the electrodes of the IMD.

In accordance with embodiments herein, the ATP therapy may be defined in part by analyzing the VT cycle length to determine a secondary delay that is at least twice the VT cycle length and determining a length of the non-stimulation segment based on the secondary delay. For example, the secondary delay corresponds to a time interval that equals the coupling interval combined with a number N of a projected VT cycle length, where the number N is two or greater. In accordance with embodiments herein, the ATP therapy is defined to enable a power source, in a low charge state, to maintain charge on a charge delivery circuit of the IMD for the ATP therapy, the low-charge state corresponding to the power source having a source impedance equal to or greater than 2000 ohms.

Figure 1B:
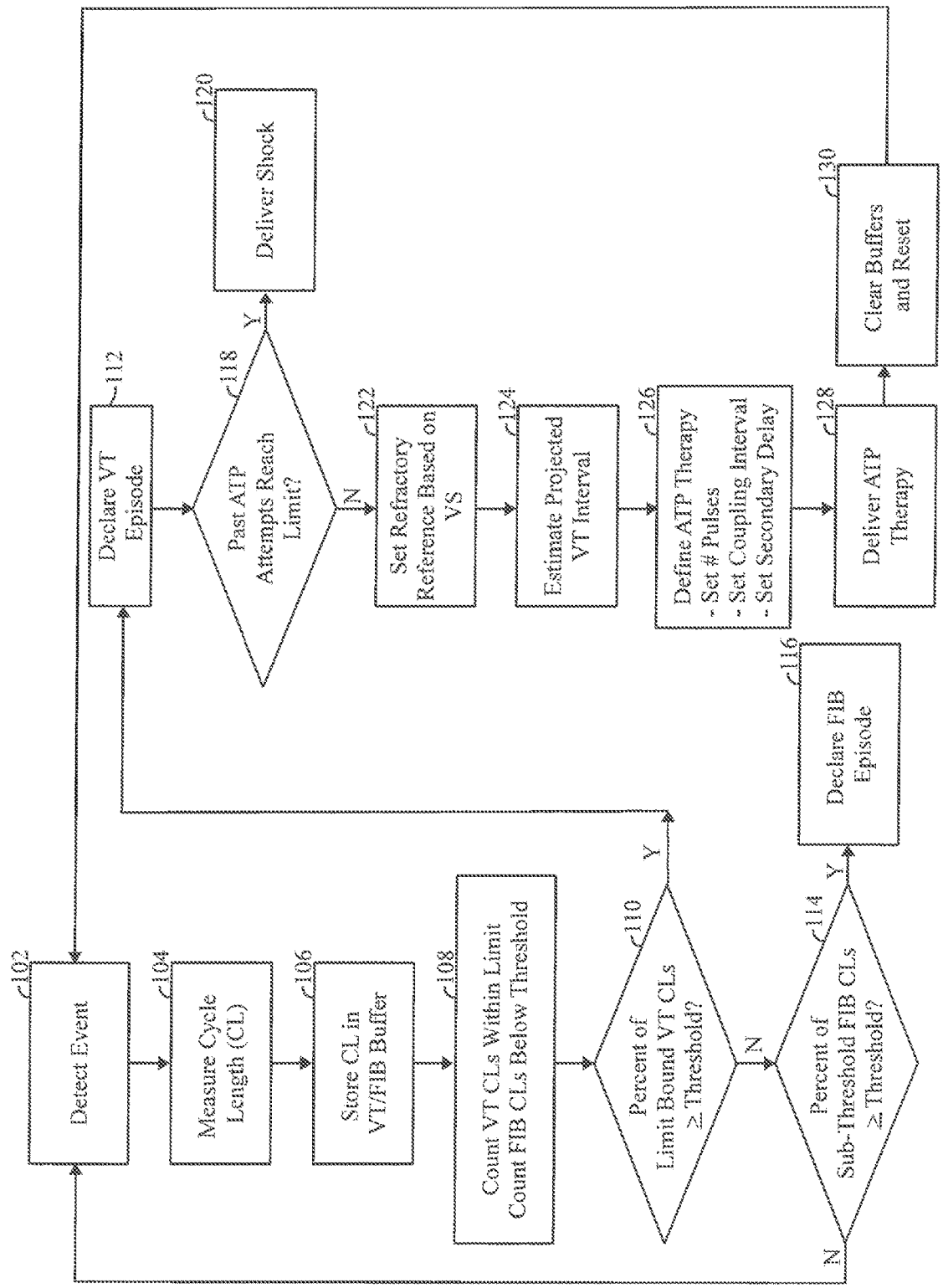
FIG. 1B illustrates a flowchart implementing a method for performing anti-tachycardia pacing according to an embodiment herein.

FIG. 1B illustrates a flowchart implementing a method for performing anti-tachycardia pacing according to an embodiment herein. FIG. 1B may represent a more detailed implementation of the method of FIG. 1A. The IMD senses cardiac signals at one or more combinations of electrodes provided on or coupled to the IMD. The cardiac signals are continuously or periodically processed by a sensing circuit, one or more processors within the IMD and/or one or more processors within an external device. In accordance with embodiments herein, the method of FIG. 1B may be implemented in response to a determination by an IMD that a patient is experiencing some type of arrhythmia involving an elevated heart rate, such as ventricular tachycardia or fibrillation. Optionally, the method of FIG. 1B may be implemented by the IMD based on other criteria, without first determining whether an arrhythmia exists.

At 102, the sensing circuit detects one or more events from cardiac signals sensed at electrodes of the IMD. The cardiac signals are representative of cardiac activity occurring in at least one chamber of the heart. For example, the sensing circuit may detect a peak of an R-wave, a peak of a T-wave, a QRS complex or other characteristic of interest within the morphology of the cardiac signal.

At 104, one or more processors of the IMD (and/or external device) measure a cycle length between the most recent event detected at 102 and a prior event detected and saved. The cycle length corresponds to an inter-event interval or event to event interval. For example, the IMD may include an interval timer that is reset each time an event is detected at 102. At 104, the one or more processors identify the current value of the interval timer, as an indication of the interval (cycle length) between the current event and the most recent prior event. The event timer is then reset and restarted. Optionally, alternative techniques may be utilized to measure the cycle length.

At 106, the one or more processors determine whether the cycle length corresponds to a ventricular tachycardia (VT) event or a fibrillation (FIB) event and saves the CL in a corresponding VT or FIB buffer memory. For example, the cycle length may be compared to a lower VT threshold and/or a FIB threshold. The processors store CLs, that are in a VT range, in a VT buffer memory and store CLs, that are in a FIB range, in a FIB buffer memory. The buffer memories may represent circular buffers in which each cycle length is stored and read out in a first-in first-out manner. The circular buffers may have a length that is defined based on a number of VT/FIB events of interest. The circular buffers store a predetermined number of successive cycle lengths to be utilized as described hereafter in connection with identifying VT episodes and FIB episodes.

It is recognized that one or more CL over a series of cardiac cycles may have a normal physiology length. Optionally, when the CL is normal (e.g., above the VT/FIB thresholds), the processors may account for the cardiac cycle in various manners. For example, when the CL is normal, the CL may be stored in both of the VT and FIB buffers, in order to track the normal CL and the point in the series of cardiac cycles where the normal CL occurred. Alternatively, the CL may not be stored in either of the VT/FIB buffers. Instead, the CL may be stored in a different memory and/or a counter maybe incremented to count the number of normal CL since the VT and/or FIB buffers were reset. Optionally, the counter may track the total number of cardiac cycles that have been analyzed since the VT and/or FIB buffers were reset.

Optionally the operations at 102-106 may be performed at one point in time for a collection of events detected over multiple cardiac cycles.

At 108, the one or more processors count the number of cycle lengths stored in the VT buffer memory that fall within predetermined limits (or exceed an upper limit). For example, the processors may count the number of VT cycle lengths, from the series of VT cycle lengths stored in the buffer memory, that are between upper and lower VT limits. The VT limits may define upper and lower limits for an interval between successive cardiac events associated with ventricular tachycardia. As one nonlimiting example, the lower VT limit may be 240 ms, while the upper VT limit may be 360 ms. By way of example, the processors may determine a count of a number of VT cycle lengths $X_{VT}$ out of a set of VT cycle lengths $Y_{VT}$ that fall within the range between the upper and lower limits.

It is recognized that the VT buffer memory may store VT cycle lengths that do not fall within the limits. Instead, some VT events may not be considered the type of VT event that warrants ATP therapy. At 108, the processors count the number of VT cycle lengths that warrant ATP therapy. The limits are applied at 108 in connection with embodiments in which a particular range of VT events are of interest, while VT events outside of the limits may not warrant ATP therapy (e.g., having longer or slower cycle lengths). Optionally, when every VT event is of interest, the limits may not be utilized at 108, but instead, at 108 the one or more processors may count the number of total VT events that occur over a number of cardiac cycles.

In addition, the processors count the number of cycle lengths stored in the FIB buffer memory that fall below an upper limit. For example, the processors may count the number of FIB cycle lengths, from the series of FIB cycle lengths stored in the buffer memory, that is less than or equal to 320 ms. The processors determine a count of a number of FIB cycle lengths $XX_{FIB}$ out of a set of FIB cycle lengths $YY_{FIB}$ that are below the upper FIB limit. It is recognized that the VT and FIB limits may be programmed to different levels and modified automatically by the IMD throughout operation, such as based upon feedback during operation or from the patient.

At 110, the one or more processors determine a ratio or percentage of the VT cycle lengths, within the VT limits, out of the total number of VT cycle lengths. The processors determine whether the ratio or percentage equals or is greater than a VT threshold (e.g., $X_{VT}/Y_{VT} \geq 0.875$). When the ratio or percentage of the VT cycle lengths (within the upper and lower VT limits) out of the total number of VT cycle lengths exceeds the threshold, flow moves to 112. Otherwise, flow continues to 114.

At 114, the one or more processors determine whether a ratio or percentage of the FIB cycle lengths, below FIB limits, equals or is greater than a FIB threshold (e.g., $XX_{FIB}/YY_{FIB} \geq 0.75$). When the ratio or percentage of the FIB cycle lengths (above the FIB limit) out of the total number of FIB cycle lengths exceeds the threshold, flow moves to 116. Otherwise, the processors determined that no fibrillation therapy or anti-tachycardia pacing therapy is warranted and flow returns to 102.

At 116, the one or more processors declare the patient to be experiencing a fibrillation episode and the IMD delivers a fibrillation shock therapy (e.g., a defibrillation shocks). Thereafter, the processors may reset the buffers, counters and other aspects, begin sensing new cardiac events and restart event detection at 102. Alternatively, the process of FIG. 1B may terminate.

Returning to 110, when flow moves to 112, the one or more processors declare the patient to be experiencing a ventricular tachycardia episode and flow continues to 118. At 118, the one or more processors compare a number of past ATP therapy attempts that have been performed by the IMD with a limit. For example, a count of ATP therapy attempts may be maintained indefinitely or for predetermined periods of time. When the number of ATP attempts reaches a limit, the processors determined that no more ATP attempts should be performed (at least in connection with the current tachycardia episode) and thus flow moves to 120. At 120, the IMD delivers a programmed shock (e.g., defibrillation shock). Optionally, the IMD may be programmed to deliver various types of therapy at 120, or to cease attempting to deliver any type of therapy.

Returning to 118, when the IMD has performed fewer than the maximum number of ATP attempts, flow moves to 122. At 122, the one or more processors identify a time at which the last ventricular event (detected at 102) was sensed VS. The processors set a refractory reference based on the last ventricular sensed event VS. The refractory reference is used in connection with ATP therapy. As explained herein, the ATP therapy is timed to have initial and subsequent pulses delivered relative to the refractory reference set at 122. The first pulse of the ATP therapy is offset from the refractory reference by a coupling interval, such as a programmed percentage of the VT cycle length.

At 124, the one or more processors estimate a projected VT interval, at which future VT events will occur unless or until a tachycardia episode is terminated. For example, the estimate of the projected VT cycle length may be based on (or equal) a mode, average or other statistical relation of the prior measured VT cycle lengths. For example, the IMD may measure and save 5-9 VT cycle lengths at 104-106. At 124, the 5-9 VT cycle lengths are utilized as a basis for the projected VT cycle length.

At 126, the one or more processors define an ATP therapy based on VT event related information collected. For example, the VT event related information includes the refractory reference of the last ventricular sense VS event determined at 122. The VT event related information also includes the projected VT cycle length estimated at 124. The VT event related information also includes a number of ATP pulses to be delivered during the ATP therapy. The ATP pulse cycle length is determined based on the projected VT cycle length. For example, the ATP pulse cycle length may be defined as a percentage of the projected VT cycle length. The ATP therapy may be defined based on various parameters, such as the number of ATP pulses per attempt, the coupling interval and the like.

At 128, the one or more processors manage delivery of the ATP therapy defined at 126. Among other things, the first ATP pulse of the ATP therapy is delayed for the coupling interval relative to the last ventricular sensed VS event. A second and subsequent pulses of the ATP therapy are staged a secondary delay following the first ATP pulse. The secondary delay is set such that the second pulse is space to follow the first ATP pulse by a time period sufficiently long to permit at least two projected VT events to occur between the first and secondary pulses, and between subsequent secondary pulses. For example, the secondary delay may space the secondary pulse to follow the first ATP pulse by at least 1.75, 1.85, 1.95, or 2 times, or another number N times the projected VT cycle length. The third and any other subsequent pulses within the ATP therapy may be spaced to follow a preceding ATP pulse by the same secondary delay. By using a common secondary delay that is at least twice as long as the projected VT cycle length, embodiments herein afford a spacing between successive ATP pulses that allows the power source to recover from a depleted condition following the first ATP pulse.

Additionally or alternatively, the spacing between the second and third pulses may be adjusted to add an additional incremental delay to the secondary delay to shift delivery of the next ATP pulse relative to the last VT event. Similarly, the spacing between the third and fourth pulses, etc., may be adjusted to add an additional incremental delay to the secondary delay. By adding an additional incremental delay to one or more of the secondary delays, the corresponding subsequent ATP pulse is delivered at a different point in time relative to the refractory time period following the most recent preceding projected VT event.

Optionally, the ATP therapy may be delivered a preset number of times at 128. Alternatively, the ATP therapy may be delivered one or more times, with an intervening sensing operation (as described in connection with FIG. 3) to determine whether the tachycardia has been terminated. In the event the tachycardia is not terminated, the ATP therapy may be repeated at 128.

At 130, the processor clears and resets the various counters and buffers related to the most recent tachycardia episode and flow returns to the start at 102.

The operations of FIG. 1B may be repeated multiple times, as separate ATP therapy attempts, in the event that an ATP therapy is not initially successful in terminating a tachyarrhythmia. During each iteration of the operations of FIG. 1, one or more parameters may be adjusted, such as based upon the number of the present ATP attempt. For example, an initial ATP attempt may utilize a first set of parameters during the determinations of FIG. 1, while second, third and/or fourth attempts may utilize different parameter sets.

Figure 2A:
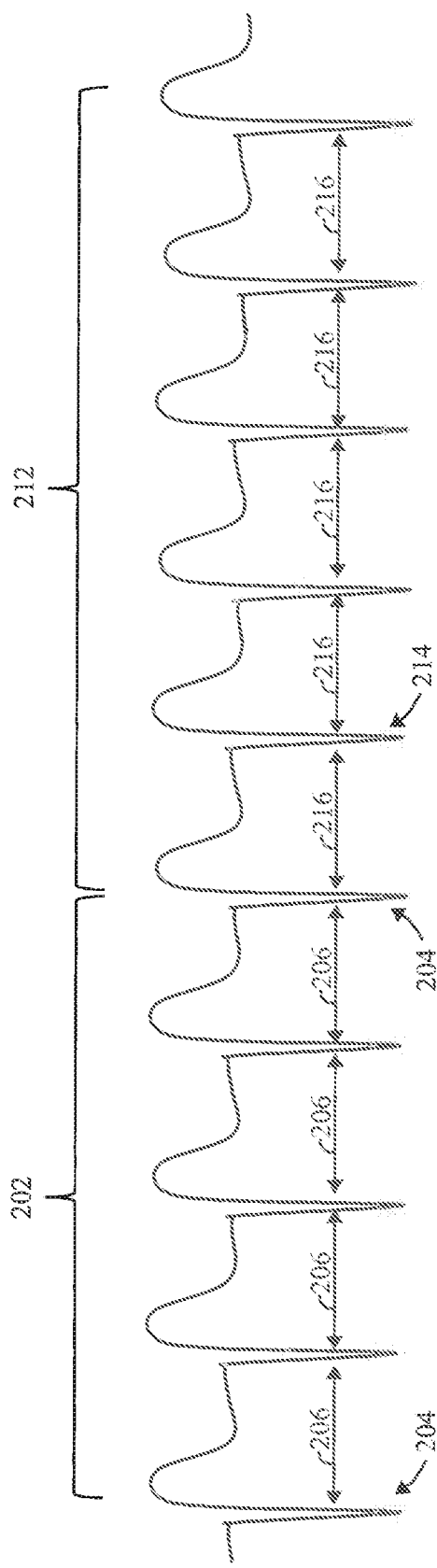
FIG. 2A illustrates a timing diagram related to sensing cardiac signals and delivering an ATP therapy in accordance with embodiments herein.

FIG. 2A illustrates a timing diagram related to sensing cardiac signals and delivering an ATP therapy in accordance with embodiments herein. In FIG. 2A, a segment of cardiac signals 202 is sensed by the electrodes of an IMD. The segment of cardiac signals 202 correspond to VT events 204 that intrinsically occur within the patient's heart. In the example of FIG. 2A, all of the events within the segment of cardiac signals 202 are illustrated to represent ventricular tachycardia events. It is recognized that not every event may have the same cycle length and not every event may be classified as a VT event. Instead, some of the events may be classified as fibrillation events or physiologic/rhythmic events (occurring at a normal interval).

In the example of FIG. 2A, all of the VT events 204 are shown to be separated by VT cycle lengths 206 that appear generally similar in length. However, it is understood that the VT cycle lengths 206 may differ at least slightly from one another. The VT cycle length 206 may vary over the course of a VT episode. As explained in connection with FIG. 1, the sensing circuit of the IMD detects the VT events 204, and the processors measure the VT cycle lengths 206. The processors store the VT cycle lengths 206 in a buffer memory (at 106) and compare a series of preceding VT events to limits (at 108). The processors determine a relation between the number of events that fall within the VT limits and the total number of events that were detected. The processors determine the ratio/percentage of VT events out of the total number of events for the period of time corresponding to the buffer memory. When the threshold is exceeded, the processors of the IMD determine that the patient is experiencing a ventricular tachycardia and ATP therapy is delivered in connection with the operations of 112-130.

FIG. 2A also illustrates a segment 212 of projected VT events 214. The projected VT events 214 are separated by a projected VT cycle length 216. The projected VT events 214 and projected VT cycle length 216 are not directly measured by the IMD, but instead are estimated based on information collected in connection with the preceding VT events 204 and VT cycle lengths 206 (as explained in connection with the operations at 112-130 in FIG. 1).

Figure 2B:
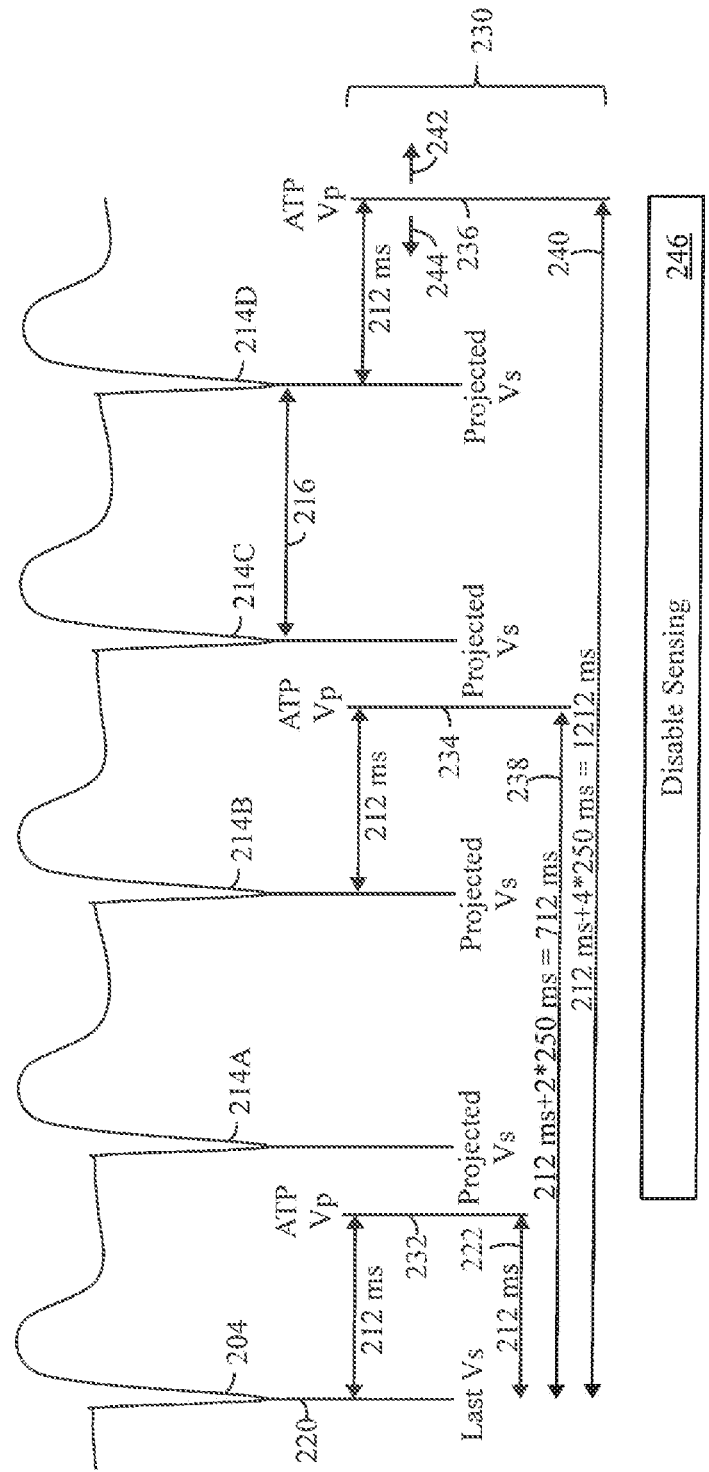
FIG. 2B illustrates the segment of projected VT events in more detail in connection with ATP therapy delivered in accordance with embodiments herein.

FIG. 2B illustrates the segment 212 of projected VT events 214 in more detail in connection with ATP therapy delivered in accordance with embodiments herein. In FIG. 2B, the first event represents a refractory reference 220 (designated at 122). The refractory reference 220 corresponds to the last sensed VT event 204, although it is understood that the refractory reference 220 may be set at another point in time relative to, but not contemporaneous with, the last sensed VT event. The last sensed VT event 204 is followed by a series of projected VT events 214 that are individually identified at 214A-214D. The projected VT events 214A-214D are also designated as "Projected VS", and are estimated to have a common VT cycle length 216. Optionally, the projected VT events 214A-214D may be estimated to be spaced apart by different VT cycle lengths in accordance with pre-defined criteria.

FIG. 2B also illustrates an ATP therapy 230, temporally aligned with the projected VT events 214A-214D. The ATP therapy 230 is noted by a series of vertical bars corresponding to the points at which ATP pulses 232, 234, 236 are delivered. The ATP therapy 230 is defined at 126 in FIG. 1B and delivered at 128. The ATP therapy 230 is programmed to include a first ATP pulse 232 followed by two secondary ATP pulses 234, 236. Optionally, the therapy 230 may include more or fewer secondary ATP pulses 234, 236. The first and second ATP pulses 232, 234 are separated by a non-stimulation segment in which no stimulation pulses are delivered. In addition, the second and third ATP pulses 234, 236 are separated by a non-stimulation segment in which no stimulation pulses are delivered.

When the ATP therapy 230 is delivered, a first ATP pulse 232 is delivered at a time spaced apart by a coupling interval 222 following the last ventricular sensed event 204 (also designated as VS). In the example of FIG. 2B, the sensed VT events 204 occur after VT cycle lengths between 220 and 300 ms. In the example of FIG. 2B, the projected VT cycle length was determined to be 250 ms. Based on a projected VT cycle length of 250 ms, the coupling interval 222 was defined to be a percentage of the projected VT cycle length (e.g., 85% or 212 ms).

The secondary pulse 234 was staged to follow the first ATP pulse 232 after a secondary delay 238. The first and second ATP pulses 232 and 234 separated by a non-stimulation segment in which no stimulation pulses are delivered. The secondary delay 238 is defined with respect to the refractory reference 220 and is set such that the secondary ATP pulse 234 is space to follow the first ATP pulse 232 by a time period sufficiently long to permit at least two projected VT events 214A, 214B to occur between the first and second ATP pulses 232, 234. For example, the secondary delay 238 may equal the coupling interval 222 combined with at least twice the projected VT cycle length 216. Accordingly, when the projected VT cycle length 216 is 250 ms, the secondary delay is set to 712 ms (212+2×250 ms). The third and any other subsequent pulses within the ATP therapy may be spaced to follow a preceding ATP pulse by the same multiple of the projected VT cycle length. For example, the secondary pulse 236 may be delivered after a secondary delay 240 which equals the coupling interval 222 combined with at least four times the projected VT cycle length 216 (e.g., 212+4×250 ms). Optionally, when additional secondary pulses are utilized, the secondary delay may be extended by a number N of the projected VT cycle length, where the number N may be an integer or a non-integer and is two or greater. For example, the secondary delay may be set to be the coupling interval i) plus 2 times the VT cycle length, ii) plus 2.5 times the VT cycle length, iii) plus 2.75 times the VT cycle length, and the like.

While the secondary delay 240 is set to correspond to a value that combines the coupling interval and a multiple of the VT cycle length, indirectly, the secondary delay 240 is defined to allow an amount of time for a charge source to restore a charge on a charge delivery circuit of the IMD. The charge delivery circuit may represent one or more charging capacitors and/or may represent the battery supply. For example, leadless pacemakers and other low power IMDs utilize batteries that are physically very small and exhibit a low initial charge. By defining the secondary delay in the manner described herein, embodiments avoid the challenges experience by conventional leadless pacemakers and other low power IMDs in connection with providing provide sustained voltages in excess of 6 V for longer pulse widths (e.g., 0.4 ms) at a high pulse rate (e.g., 160 ppm or spaced at about 375 ms intervals). Instead, during delivery of ATP therapy in accordance with embodiments herein, the leadless pacemakers and other low energy devices are afforded a recovery interval, during the secondary delay, to recover from a voltage drop (e.g., down to about 3 volts across the electrodes) back to a substantially full voltage potential (e.g., in excess of 6 volts across the electrodes).

Optionally, the timing for the secondary pulses 234, 236 may be shifted forward or backward in time by an additional incremental delay 242, 244. The increase/decrease by the incremental delay 242, 244 may be managed to move the secondary pulse 236 away from a tissue refractory state following the immediately preceding projected VT event 214D.

In the example of FIG. 2B, the VT events 214A-214D are characterized as "projected" as the sensing circuit of the IMD is disabled for the corresponding non-sensing time period 246. Following the non-sensing time period 246, the sensing circuit is again enabled and cardiac signals are sensed and analyzed by the IMD. The IMD determines whether the patient is still experiencing a ventricular tachycardia, or alternatively whether the ATP therapy has terminated the VT. When the VT is not terminated, the IMD may repeat the ATP therapy. As one example, the IMD may collect a new series of sensed ventricular events, calculate a new projected VT cycle length and a new ATP therapy. Alternatively, the IMD may utilize the previously determined projected VT cycle length and instead adjust the coupling interval and/or secondary delays. For example, during a second attempt at ATP therapy, the coupling interval may be assigned as a higher percentage (e.g., 90%) of the projected VT cycle length. Additionally or alternatively, the secondary delays may be set as non-integer multiples of the projected VT cycle length (e.g., 2.1, 2.5, etc.). In the event that a second, third or later attempt at ATP therapy is unsuccessful, the IMD may deliver a defibrillation shock (e.g., 120 in FIG. 1).

Table 1 below sets forth an example of various programmable parameters that may be utilized in connection with different ATP therapy attempts. In the following Table 1, the first column (ATP Attempts) corresponds to a number of the present ATP attempt, for which the subsequent parameters are to be used. The second column corresponds to a $X_{VT}/Y_{VT}$ VT Detection parameter used at 110 regarding the VT threshold ratio between the number of VT events detected and the number of VT events having a VT cycle length within the VT limits/range of interest. The third column corresponds to a $X_{FIB}/Y_{FIB}$ VF Detection parameter utilized at 114 regarding the FIB threshold ratio between the number of FIB events detected and the number of FIB events having an FIB cycle length below the FIB threshold. The fourth column corresponds to the parameter used at 118 to define the number of ATP attempts that will be delivered before delivering a shock (at 120). The fifth column corresponds to a parameter that sets the number of ATP pulses used during an ATP therapy. The sixth column corresponds to a coupling interval parameter that sets the percentage of the VT cycle length to be utilized as the coupling interval. The last column corresponds to a VT range parameter used at 108 to define the limitations of the VT cycle lengths to count interconnection with ATP therapy.

For example, during the first ATP attempt, the determination at 110 will determine whether seven out of the last eight VT events exhibited a VT cycle length that falls within a range between limits of 240 ms and 360 ms. During the first ATP attempt, the determination at 114 will determine whether 24 out of the last 32 fibrillation events exhibited a fibrillation rate of less than a threshold (320 ms). During the first ATP attempt, one ATP pulse will be delivered as the ATP therapy at a point in time following a coupling interval that is 88% of the projected VT cycle length.

For example, during the third ATP attempt, the determination at 110 will determine whether three out of the last four VT events exhibited a VT cycle length that falls within a range between limits of 240 ms and 360 ms. During the third ATP attempt, the determination at 114 will determine whether 24 out of the last 32 fibrillation events exhibited a fibrillation rate of less than a threshold (320 ms). During the third ATP attempt, three ATP pulses will be delivered as the ATP therapy, with the first ATP pulse 232 delivered following a ATP pulse 232 that is 81% of the projected VT cycle length and with the second and third ATP pulses 234, 236 spaced apart as shown in FIG. 2B.

TABLE 1

ALGORITHM 1: PROGRAMMABLE PARAMETERS

| ATP Attempt | $X_{VT}/Y_{VT}$ VT detection | $X_{FIB}/Y_{FIB}$ VF detection | Number of ATP attempts | Number of ATP pulses per Attempt | Coupling Interval (Percent Cycle length) | VT range (ms) |
|---|---|---|---|---|---|---|
| 1 | 7/8 | 24/32 | 4 | 1 | 88% | 240 > Intervals > 360 |
| 2 | 3/4 | 24/32 | 4 | 2 | 85% | 240 > Intervals > 360 |
| 3 | 3/4 | 24/32 | 4 | 3 | 81% | 240 > Intervals > 360 |
| 4 | 3/4 | 24/32 | 4 | 4 | 78% | 240 > Intervals > 360 |

Figure 3:
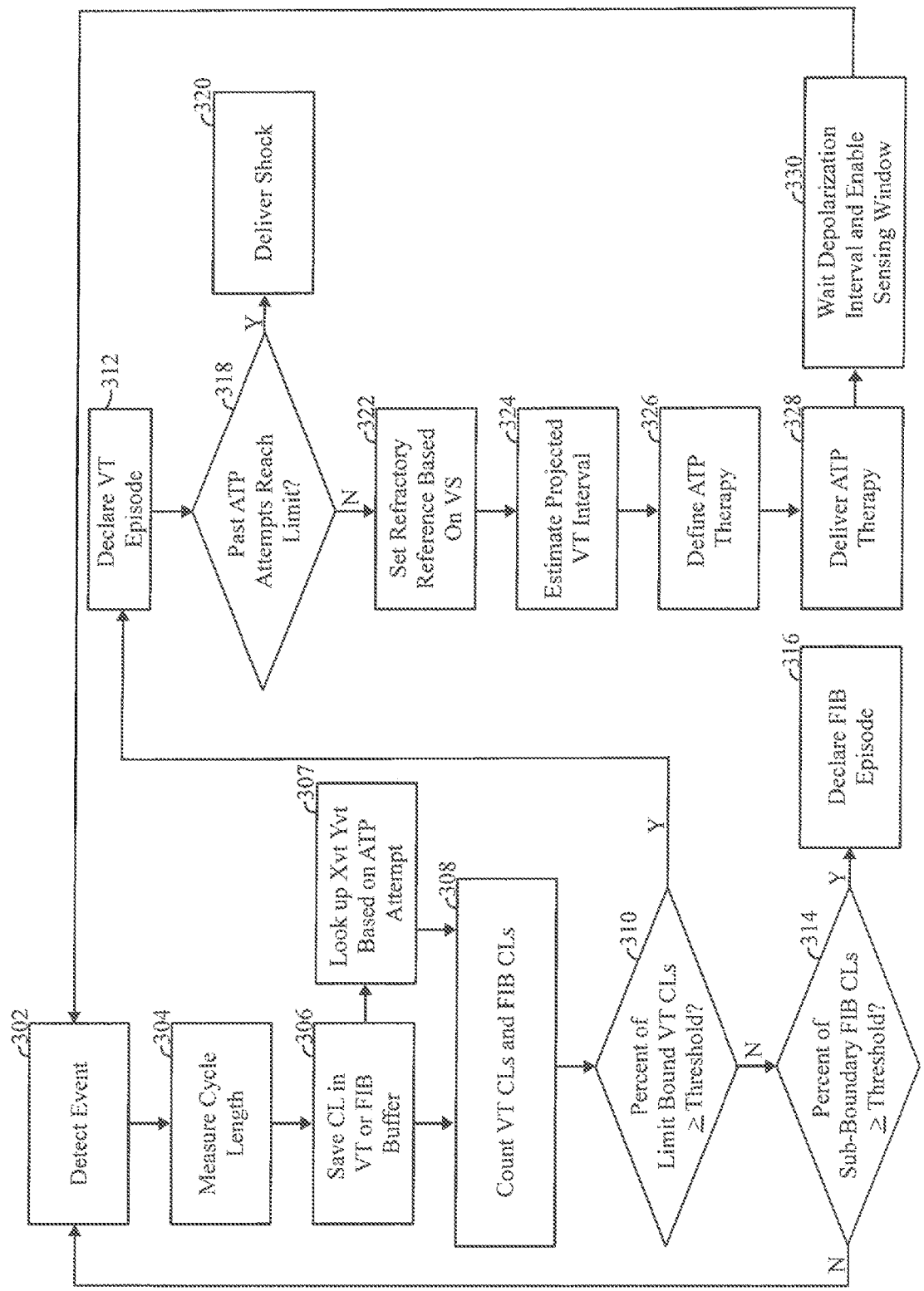
FIG. 3 illustrates a flowchart implementing a method for performing anti-tachycardia pacing according to an embodiment herein.

FIG. 3 illustrates a flowchart implementing a method for performing anti-tachycardia pacing according to an embodiment herein. Throughout operation, the IMD senses cardiac signals at one or more combinations of electrodes provided on or coupled to the IMD. The cardiac signals are continuously or periodically processed by a sensing circuit, one or more processors within the IMD and/or one or more processors within an external device. In accordance with embodiments herein, the method of FIG. 3 may be implemented in response to a determination by an IMD that a patient is experiencing some type of arrhythmia involving an elevated heart rate, such as ventricular tachycardia or fibrillation. Optionally, the method of FIG. 3 may be implemented by the IMD based on other criteria, without first determining whether an arrhythmia exists.

At 302, the sensing circuit detects an event from cardiac signals sensed at electrodes of the IMD. As noted herein, the sensing circuit may detect a peak of an R-wave, a peak of a T-wave, a QRS complex or other characteristic of interest within the morphology of the cardiac signal. At 304, one or more processors of the IMD (and/or external device) measure a cycle length between the most recent event detected at 302 and a prior event detected and saved. At 306, the one or more processors determine whether the cycle length corresponds to a ventricular tachycardia (VT) event or a fibrillation (FIB) event and saves the CL in a corresponding VT or FIB buffer memory.

After the operation at 306, flow branches along two paths, namely 307 and 308. The operations at 307 and 308 may be performed together or as alternatives.

At 307, the one or more processors lookup a number of VT cycle lengths $X_{VT}$ that fall within the predetermined limits. The processors also lookup the total number of VT cycles over a predetermined period of time and a ratio between the $X_{VT}$ and $Y_{VT}$. The lookup operation at 307 is performed based on the current ATP attempt number. As noted herein, multiple ATP attempts may be performed. During the current iteration through the operations of FIG. 3, the lookup operation at 307 is performed based on the current ATP attempt number.

At 308, the one or more processors count the number of cycle lengths stored in the VT buffer memory that fall within predetermined limits (or exceed an upper limit). As noted in connection with FIG. 1, the processors may determine a count of a number of VT cycle lengths $X_{VT}$ out of a set of VT cycle lengths $Y_{VT}$ that fall within the range between the upper and lower limits. In addition, the processors count the number of cycle lengths stored in the FIB buffer memory that fall below an upper limit. As noted above in connection with FIG. 1, the processors may determine a count of a number of FIB cycle lengths $XX_{FIB}$ out of a set of FIB cycle lengths $YY_{FIB}$ that are below the upper FIB limit.

At 310, the one or more processors determine whether a ratio or percentage of the VT cycle lengths, within the VT limits, out of the total number of VT cycle lengths. The processors determine whether the ratio or percentage equals or is greater than a VT threshold (e.g., $X_{VT}/Y_{VT} \geq 0.875$). When the ratio or percentage of the VT cycle lengths (within the upper and lower VT limits) out of the total number of VT cycle lengths exceeds the threshold, flow moves to 312. Otherwise, flow continues to 314.

At 314, the one or more processors determine whether a ratio or percentage of the FIB cycle lengths, below FIB limits, equals or is greater than a FIB threshold (e.g., $XX_{FIB}/YY_{FIB} \geq 0.75$). When the ratio or percentage of the FIB cycle lengths (above the FIB limit) out of the total number of FIB cycle lengths exceeds the threshold, flow moves to 316. Otherwise, the processors determined that no fibrillation therapy or anti-tachycardia pacing therapy is warranted and flow returns to 302.

At 316, the one or more processors declare the patient to be experiencing a fibrillation episode and the IMD delivers a fibrillation shock therapy (e.g., a defibrillation shocks). Thereafter, the process may reset the buffers, counters and other aspects, begin sensing new cardiac events and restart event detection at 302. Alternatively, the process may terminate.

Returning to 310, when flow moves to 312, the one or more processors declare the patient to be experiencing a ventricular tachycardia episode and flow continues to 318. At 318, the one or more processors compare a number of past ATP therapy attempts that have been performed by the IMD with a limit. When the number of ATP attempts reaches a limit, the processors determined that no more ATP attempts should be performed (at least in connection with the current tachycardia episode) and thus flow moves to 320. At 320, the IMD delivers a programmed shock (e.g., defibrillation shock).

Returning to 318, when the IMD has performed fewer than the maximum number of ATP attempts, flow moves to 322. At 322, the one or more processors identify a time at which the last ventricular event (detected at 302) was sensed VS. The processors set a fiducial or refractory reference based on the last ventricular sensed event VS. The refractory reference is used in connection with ATP therapy. As explained herein, the ATP therapy is timed to have first and secondary pulses delivered relative to the refractory reference.

At 324, the one or more processors estimate a projected VT interval, at which future VT events will occur unless or until a tachycardia episode is terminated. As noted above in connection with FIG. 1, the estimate of the projected VT cycle length may be based on (or equal) a mode, average or other statistical relation of the prior measured VT cycle lengths. At 326, the one or more processors define an ATP therapy based on VT event related information collected from the patient. The VT event related information includes the refractory reference, the projected VT cycle length, an ATP pulse cycle length and/or a number of ATP pulses. The ATP pulse cycle length is determined based on the projected VT cycle length. For example, the ATP pulse cycle length may be defined as a percentage of the projected VT cycle length.

At 328, the one or more processors manage delivery of the ATP therapy defined at 326. Among other things, the first ATP pulse of the ATP therapy is delayed for an coupling interval relative to the last ventricular sensed VS event. In the embodiment of FIG. 3, the ATP therapy may be limited to a single first ATP pulse that is delivered at 328. Alternatively, the ATP therapy may be defined as described in connection with FIG. 2B to include a first ATP pulse followed by one or more secondary ATP pulses. After the ATP therapy is delivered, flow moves to 330.

At 330, the one or more processors delay operation until a depolarization timer times out. The depolarization timer is set for a depolarization interval which may be preprogrammed or adjusted throughout operation. The depolarization interval corresponds to a period of time during which the pacing/sensing electrodes on the IMD are polarized by the ATP pacing pulse(s). Immediately following delivery of an ATP pulse, the pacing/sensing electrodes are polarized and unable to sense intrinsic cardiac signals. The depolarization interval affords a time period for the electrodes to settle and depolarize. When the depolarization interval terminates, flow returns to the start at 302 where the next event is detected.

Figure 4A:
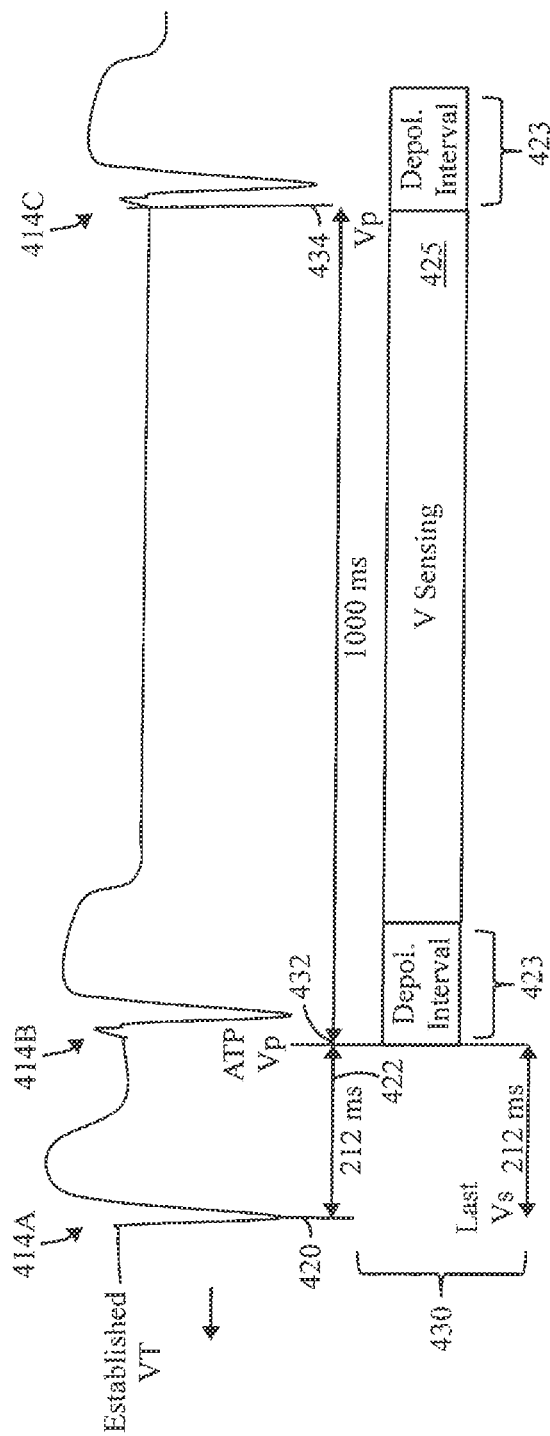
FIG. 4A illustrates a series of cardiac events from one type of physiologic response to ATP that occur during delivery of an ATP therapy in accordance with the embodiment of FIG. 3.

FIG. 4A illustrates a series of cardiac events 414A-414C from one type of physiologic response to ATP that occur during delivery of an ATP therapy 430 in accordance with the embodiment of FIG. 3. The cardiac event 414A, corresponding to a VT event, is detected at 302, and a VT cycle length is measured at 304, and is processed at 306-324 to define a corresponding ATP therapy. The initial VT event 414A is used as the basis to set as a refractory reference 420 (at 322) utilized in the ATP therapy 430. The VT event 414A is followed by a second VT event 414B.

FIG. 4A also illustrates the timing of the ATP therapy 430, temporally aligned with the VT events 414A-414B. The ATP therapy 430 includes a first ATP pulse 432 noted by a vertical bar corresponding to the points at which first ATP pulse 432 is delivered. The ATP therapy 430 is defined at 326 in FIG. 3 and delivered at 328. The ATP therapy 430 is programmed to include a first ATP pulse 432, and if necessary additional ATP pulses (not shown). The first ATP pulse 432 is delivered at a time spaced apart by a coupling interval 422 following the last ventricular sensed event 414A (also designated as VS). In the example of FIG. 4A, the projected VT cycle length was determined to be 250 ms, and the coupling interval 422 was defined to be a percentage of the projected VT cycle length (e.g., 85% or 212 ms).

After the first ATP pulse 432 is delivered, a depolarization timer is set for a depolarization interval 423 (corresponding to 330 in FIG. 3). When the depolarization interval 423 ends, the IMD opens a sensing window 425 to listen for cardiac signals in connection with a next cardiac event (corresponding to 302 in FIG. 3). In the example of FIG. 4A, no cardiac event occurs (or is sensed) following the first ATP pulse 432. Instead, an escape interval timer times out after a 1000 ms delay following the first ATP pulse 432. When the escape interval timer times out, the IMD delivers a next ventricular pacing pulse 434 to initiate a ventricular event 414C. After the ventricular pacing pulse 434, the depolarization timer is reset to wait for the depolarization interval 432 after which another sensing window is opened. Thereafter, flow returns to 302 in FIG. 3.

Figure 4B:
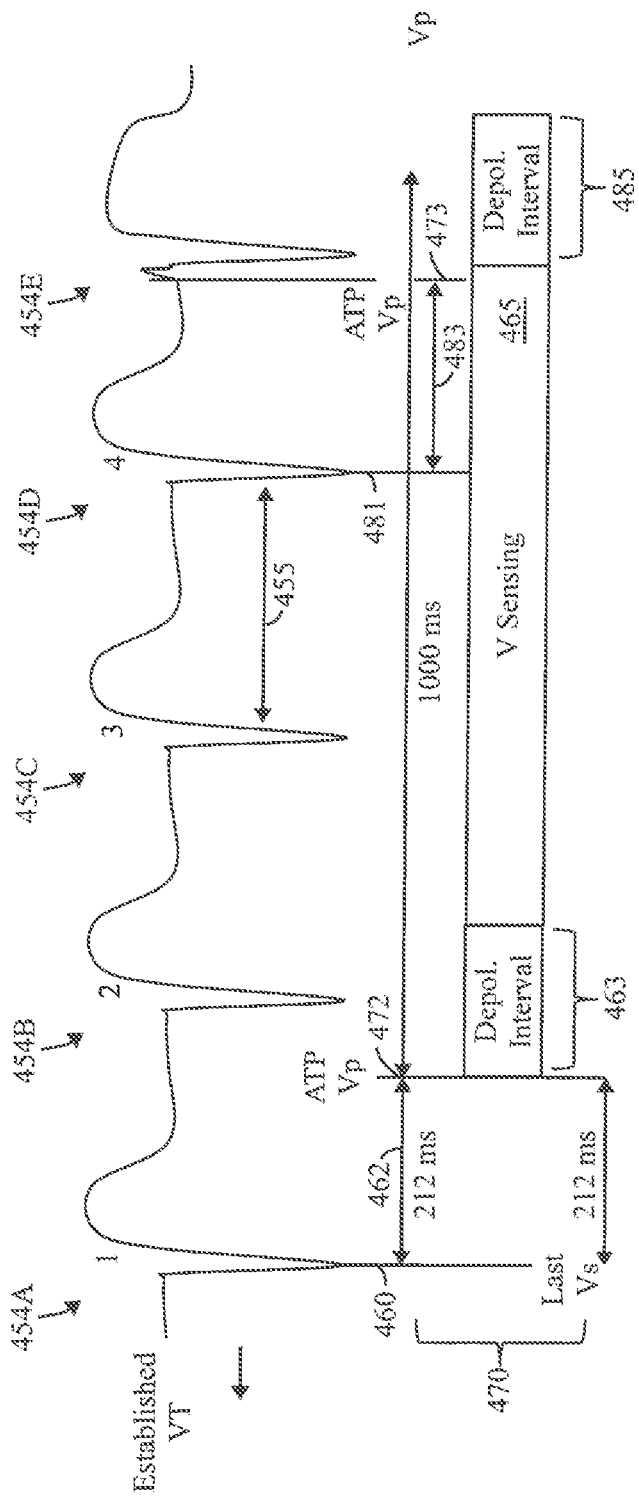
FIG. 4B illustrates a series of cardiac events from another physiologic response to ATP that occur during delivery of an ATP therapy in accordance with the embodiment of FIG. 3.

FIG. 4B illustrates a series of cardiac events 454A-454E from another physiologic response to ATP that occur during delivery of an ATP therapy 470 in accordance with the embodiment of FIG. 3. The series includes an initial VT event 454A that is used to set a refractory reference 460 (at 322). The coupling interval 462 follows the refractory reference 460, after which a first ATP pulse 472 is delivered. When the first ATP pulse 472 is delivered, a depolarization interval 463 is set. After expiration of the depolarization interval 463, a sensing window 465 is opened and the IMD senses cardiac signals for the period of time corresponding to the sensing window 465. In the present example, two VT events 454C and 454D are detected during the sensing window 465, although it is understood that more or fewer events may be sensed based upon the length of the interval between successive events.

When the sensing window 465 is closed, flow returns to 302 in FIG. 3 where the one or more cardiac signals are processed. In the example of FIG. 4B, the first ATP pulse 472 did not achieve capture and did not have an effect on the tachyarrhythmia. Thus, during the next iteration at 302, the VT events 454C and 454D are detected and the cycle length 455 there between is measured at 304. Thereafter, the operations of FIG. 3 are repeated utilizing the cycle length 455 measured between events 454C and 454D. A new projected VT interval is estimated at 324 based on the VT interval between the VT events 454C and 454D. In one example, the projected VT interval for the ATP therapy may be based solely on the cycle length 455 between the VT events 454C and 454D. During the second iteration through the determination at 310, the threshold utilized at 310 may be changed. For example, the threshold may be changed such that a single VT cycle length within a predetermined range may be sufficient to trigger initiation of the next ATP pulse. For example, at 310, the determination may be made as to whether the VT interval is between 220 and 300 ms. If so, flow branches to 312 and the processors declare that the VT episode continues.

Optionally, the determination at 310 may search for 2 out of 3, or 3 out of 4 VT events, etc. within the predetermined limits. When the desired number of VT events are detected within the predetermined limits, flow moves from 312 through 328. A new refractory reference 481 is set corresponding to the VT event 454D and a new coupling interval 483 is defined starting at the refractory reference 481. After the coupling interval 483, the next ATP pulse 473 is delivered, followed by a new depolarization interval 485. The first and second ATP pulses 472, 473 are separated by a non-stimulation segment in which no stimulation pulses are delivered.

The coupling interval 483 may be defined as a percentage of the VT interval or a percentage of an average or mode over multiple VT intervals. The relation between the coupling interval 483 and the VT interval may be maintained constant for all ATP pulses. Alternatively, the relation between the coupling interval 483 and the VT interval may be changed in connection with different ATP pulses within a single ATP therapy. For example, during the first iteration through FIG. 3, when calculating the start time of the first ATP pulse 472, the coupling interval 462 may be set to be 85% of the projected VT interval. When the first ATP pulse 472 does not terminate the tachyarrhythmia, a different percentage may be utilized in connection with the next coupling interval 483 when calculating the start time of the second ATP pulse 473. For example, the coupling interval 483 may be set to be 75%, 90%, etc. of the projected VT interval). Optionally, the coupling interval may be scanned by decreasing percentage used by the coupling interval during detection of each successive VT event to increase a probability of when the surrounding tissue is in an excitable state (the excitable gap).

Table 2 below sets forth an example of various programmable parameters that may be utilized in connection with different ATP therapy attempts according to the operations of at least FIG. 3. In Table 2, no parameter is defined in connection with the number of pulses per attempt as a single pulse is delivered during each ATP attempt. Otherwise, the columns in Table 2 correspond to the parameters described above in connection with Table 1, but with at least some different parameters. For example, during the first ATP attempt, the determination at 310 will determine whether seven out of the last eight VT events exhibited a VT cycle length that falls within a range between limits of 240 ms and 360 ms. However, during the second, third and fourth ATP attempts, the determination at 310 will only consider whether a single VT event exhibited a VT cycle length within the range of 240 ms to 360 ms. As explained herein, a single VT event may be utilized to determine the VT cycle length in accordance with embodiments that perform sensing following delivery of an ATP pulse (FIGS. 3, 4A and 4B). The remaining parameters in Table 2 may be the same as or different from the parameters in Table 1.

TABLE 2

ALGORITHM 2: PROGRAMMABLE PARAMETERS

| ATP Attempt | $X_{VT}/Y_{VT}$ VT detection | $X_{FIB}/Y_{FIB}$ VF detection | Number of ATP attempts | Coupling Interval (Percent Cycle length) | VT range (ms) |
|---|---|---|---|---|---|
| 1 | 7/8 | 24/32 | 4 | 88% | 240 > Intervals > 360 |
| 2 | 1/1 | 24/32 | 4 | 85% | 240 > Intervals > 360 |
| 3 | 1/1 | 24/32 | 4 | 81% | 240 > Intervals > 360 |
| 4 | 1/1 | 24/32 | 4 | 78% | 240 > Intervals > 360 |

Implantable Medical Device

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Figure 5:
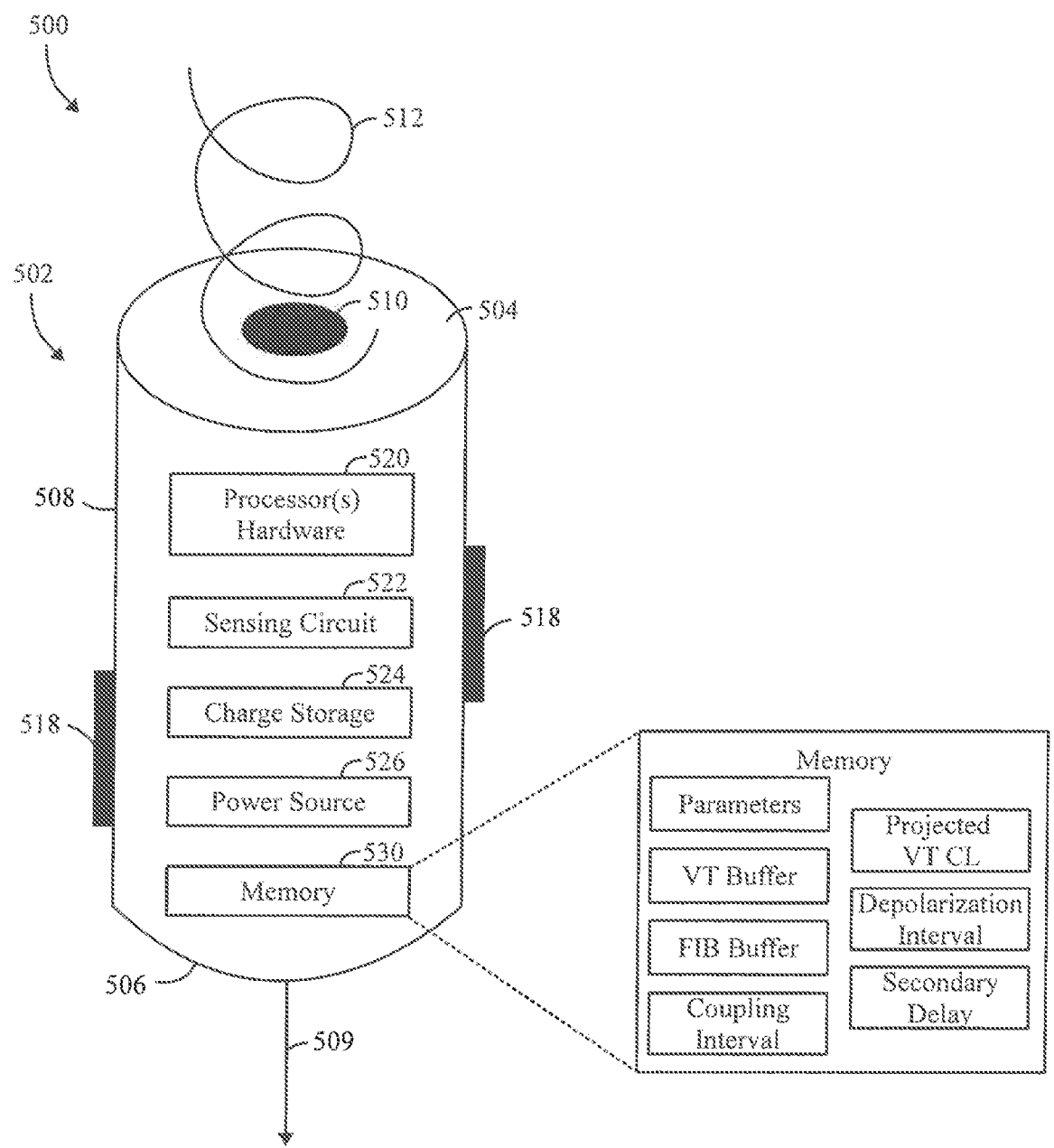
FIG. 5 illustrate an IMD formed in accordance with embodiments herein.

FIG. 5 illustrate an IMD 500 formed in accordance with embodiments herein. The IMD 500 comprises a housing 502 having a proximal base 504, a distal top end 506, and an intermediate shell 508 extending between the proximal base 504 and the distal top end 506. The shell 508 is elongated and tubular in shape and extends along a longitudinal axis 509. FIG. 5 illustrates a side perspective view of the IMD 500 oriented with the base 504 facing upward to illustrate an electrode 510 and a fixation helix 512 in more detail. The fixation helix 512 is also provided directly on the housing 502 of the IMD 500 and may be configured as a screw with a large pitch (e.g. length between adjacent turns), large diameter and may have a length that is relatively short. One or more anode electrodes 518 may be provided. The anode electrode(s) 518 may be located along one or more sides of the shell 508, and/or on the top end 506 of the IMD 500. The housing 502 is formed of a conductive material that is partially coated with an insulation layer. The anode electrode(s) 518 may represent a portion of the housing 502 that is not covered with the insulation coating. Alternatively, the electrode(s) 518 may be separate electrodes assembled onto the housing 502 and/or connected to the electronics of the IMD 500 through a header.

In the example of FIG. 5, the electrodes 510, 518 are provided on or as part of the housing 502 to form a leadless IMD. Alternatively, a lead-based IMD may be utilized in which one or more leads may be connected to the IMD 500 through a header (not shown), where the one or more leads include one or both of the electrodes 510, 518.

The IMD 500 includes various combinations of components for the operation of an IMD, as described in the patents and applications referenced herein and as known in the field. Relative to embodiments herein, the IMD 500 includes one or more processors 520, a sensing circuit 522, a charge storage circuit 524, an power source (battery) 526, telemetry circuit 528 and memory 530, all of which are hermetically sealed within the housing 502. The memory 530 is shown in an enlarged detail to better illustrate data, parameters and other information that are stored in the memory 530 and utilized in connection with embodiments herein. The memory 530 includes program instructions that, when executed by the processors 520, perform the operations described herein. Optionally, the program instructions may represent firmware and the processors may represent hardware that executes the firmware to perform the operations described herein.

The memory 530 stores parameters utilized in connection with the operations herein, such as the parameters discussed in connection with tables 1 and 2. The memory 530 includes one or more VT memory buffers and FIB memory buffers to store VT cycle length and FIB cycle length that are analyzed in accordance with embodiments herein. The memory 530 stores projected a VT cycle length that are calculated based on the VT cycle length measured from VT events. The memory 530 stores one or more coupling intervals that are calculated from VT cycle length and/or projected VT cycle lengths. The memory 530 also stores a depolarization interval utilized in connection with some embodiments for determining when to enable the sensing circuit following delivery of an ATP pulse. The memory 530 also stores a secondary delay that is formed from a combination of the coupling interval and multiples of the projected VT cycle length, where the secondary delay is utilized to time secondary ATP pulses.

The sensing circuit 522 senses intrinsic cardiac signals sensed at the electrodes 518, where the cardiac signals are representative of cardiac activity occurring in at least one chamber of the heart (e.g., the chamber wherein the IMD 500 is located or in a lead-based IMD, the chamber where the electrodes are located). The sensing circuit 522 may perform event detection to detect events in the sensed cardiac signals. For example, the sensing circuit 522 may apply threshold detection to only pass sensed signals above select thresholds. Alternatively, the processors 520 may analyze the sensed cardiac signals and perform event detection.

The sensing circuit 522 is enabled and disabled at different points during detection of VT events and delivery of ATP therapy. In accordance with some embodiments herein, the sensing circuit 522 is disabled during the entire ATP therapy. In accordance with other embodiments, the sensing circuit 522 is disabled for short intervals within an ATP therapy and enabled at other intervals within the ATP therapy. For example, the one or more processors 520 may disable the sensing circuit 522 for a depolarization interval following delivery of the first ATP pulse, and enable the sensing circuit 522 to sense cardiac signals after termination of the depolarization interval and before delivery of the second ATP pulse.

The charge storage circuit 524 stores high or low energy amounts to be delivered in one or more ATP pacing/stimulus pulses. The electrodes 510, 518 are configured to be joined to the charge storage circuit 524. The electrodes 510, 518 may be used to deliver lower energy or high energy stimulus, such as pacing pulses, cardioverter pulse trains, defibrillation shocks and the like. The electrodes 510, 518 may also be used to sense the cardiac signals, including physiologic and pathologic behavior and events and provide sensed signals to the sensing circuit 522.

The one or more processors 520 execute the program instructions in the memory 530 to perform the operations described herein, including analyzing the VT cycle length to define an anti-tachycardia pacing (ATP) therapy that includes a first coupling interval. The processors 520 deliver a first ATP pulse that is spaced the coupling interval after a reference refractory VT event sensed at the electrodes and deliver a second ATP pulse following the first ATP pulse by a non-stimulation segment that is at least 1.75 times a projected VT cycle length. Optionally, the processors 520 analyze the VT cycle length to determine the secondary delay that is at least twice the VT cycle length and determining a length of the non-stimulation segment based on the secondary delay. For example, the secondary delay corresponds to a time interval that equals the coupling interval combined with a number N of a projected VT cycle length. By way of example, the number N is two or greater. The first coupling interval may be set as a percentage of the projected VT cycle length. The first coupling interval is set to time the first ATP pulse to occur during a non-refractory state of tissue proximate to the electrodes of the IMD. The one or more processors 520 may determine a length of the non-stimulation segment based on a second coupling interval related to a VT cycle length of at least two VT events that occur after delivery of the first ATP pulse. More specifically, an ending point of the non-stimulation segment may be set to correspond to an ending point of the second coupling interval.

The power source (battery) 526 represents a low-charge power source. The power source includes terminals connected to the charge storage circuit 524 in order to charge the charge storage circuit 524 in connection with various types of therapy including ATP therapy. For example, the power source 526 includes one or more batteries having terminals connected to a charge storage circuit, the power source exhibiting a power state in which a source impedance, across the terminals of the power source, is equal to or greater than 2000 ohms when the power source is connected to a charge storage circuit.

In accordance with embodiments herein, the IMD may represent a leadless pacemaker that includes a very small power source 526 that, even when in a new condition, exhibits a low charge state. Alternatively, the IMD may represent a lead based IMD or larger leadless IMD that includes a larger power source 526 that, when in a new condition, exhibits a relatively higher charge state. However, over the life of the IMD, the charge state of the power source 526 will diminish to a low charge state at some point during the life.

In accordance with embodiments herein, the ATP therapy is defined to enable power sources 526 in a low charge state to maintain charge on the charge delivery circuit 524, the low-charge state corresponding to the power source having a source impedance equal to or greater than 2000 ohms. By way of example, the ATP therapy includes at least three ATP pulses having an amplitude of at least 6 V and a pulse width of at least 0.4 ms.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:
1. An implantable medical device, comprising:
a housing coupled to electrodes;
an power source within the housing;
memory, within the housing, to store storing program instructions;
a sensing circuit to sense cardiac signals from the electrodes, the cardiac signals representative of a ventricular tachycardia (VT) episode that includes at least a select number of VT events having corresponding VT cycle lengths; and
one or more processors within the housing, wherein, responsive to execution of the program instructions, the one or more processors configured to:
analyze the VT cycle length to define an anti-tachycardia pacing (ATP) therapy that includes a first coupling interval;

set the first coupling interval, based on the VT cycle length, to time a first ATP pulse to occur during a non-refractory state of tissue proximate to the electrodes;

deliver the first ATP pulse that is spaced the coupling interval after a reference refractory VT event sensed at the electrodes; and deliver a second ATP pulse following the first ATP pulse by a non-stimulation segment that is at least one and three-quarters (1.75) times a projected VT cycle length.

2. The device of claim 1, wherein the power source includes one or more batteries having terminals connected to a charge storage circuit, the power source exhibiting a power state in which a source impedance, across the terminals of the power source, is equal to or greater than 2000 ohms when the power source is connected to a charge storage circuit.

3. The device of claim 2, wherein the implantable medical device is a leadless pacemaker with the electrodes provided on or as part of the housing.

4. The device of claim 1, wherein the one or more processors are configured to analyze the VT cycle length to determine the projected VT cycle length and to determine a secondary delay that is at least twice the projected VT cycle length and determine a length of the non-stimulation segment based on the secondary delay.

5. The device of claim 1, wherein the secondary delay corresponds to a time interval that equals the coupling interval combined with a number N of the projected VT cycle length.

6. The device of claim 1, wherein the first coupling interval is a percentage of the projected VT cycle length.

7. The device of claim 1, wherein the one or more processors are configured to define the ATP therapy to include at least three ATP pulses having an amplitude of at least 6 V and a pulse width of at least 0.4 ms.

8. The device of claim 1, wherein the sensing circuit is disabled for a depolarization interval following delivery of the first ATP pulse and, after termination of the depolarization interval, the sensing circuit is enabled to sense cardiac signals, between the first and second ATP pulses.

9. The device of claim 8, wherein the one or more processors are configured to time delivery of the second ATP pulse based on at least two VT events sensed after termination of the depolarization interval.

10. The device of claim 9, further comprising determining a length of the non-stimulation segment based on a second coupling interval related to a VT cycle length of the at least two VT events sensed after termination of the depolarization interval.

11. The device of claim 1, wherein the one or more processors are configured to deliver at least first and second ATP therapies and to to implement a scan for the first coupling interval by decreasing the first coupling interval between the first and second ATP therapies to increase a probability of pacing while the tissue is in an excitable non-refractory state.

12. The device of claim 1, wherein the one or more processors are configured to automatically determine and set the first coupling interval based on the VT cycle length.

* * * * *